United States Patent [19]

Martin

[11] Patent Number: 5,226,880

[45] Date of Patent: * Jul. 13, 1993

[54] ANGIOPLASTY CATHETER WITH BALLOON RETAINER

[75] Inventor: Geoffrey S. Martin, Mississauga, Canada

[73] Assignee: Vas-Cath Incorporated, Ontario, Canada

[ * ] Notice: The portion of the term of this patent subsequent to May 13, 2008 has been disclaimed.

[21] Appl. No.: 476,061

[22] Filed: Jan. 30, 1990

[30] Foreign Application Priority Data

Jan. 31, 1989 [CA] Canada ................................ 589694

[51] Int. Cl.⁵ .............................................. A61M 29/02
[52] U.S. Cl. ...................................... 604/99; 604/96; 606/194
[58] Field of Search ................................ 604/96–103; 606/192, 194

[56] References Cited

U.S. PATENT DOCUMENTS

| 1,690,995 | 11/1928 | Pratt | 606/192 |
| 3,435,826 | 4/1969 | Fogarty | 606/194 |
| 4,637,396 | 1/1987 | Cook | 604/99 |

Primary Examiner—Stephen C. Pellegrino
Attorney, Agent, or Firm—Rogers & Scott

[57] ABSTRACT

An angioplasty catheter is disclosed having an elongate main body defining guide wire and fluid supply lumens and terminating at a distal end in a tapered tip. The fluid supply lumen is closed at the tip and the guide wire lumen extends to the tip for receiving a Seldinger wire to guide the catheter during insertion procedures. The main body defines a side opening meeting the supply lumen near the tip and a balloon is sealed to the main body near the tip and contains the side opening. The balloon has a membrane of inelastic material having a defined shape when inflated by fluid pressure applied through the supply lumen, and an elastic sheath covering the membrane.

13 Claims, 3 Drawing Sheets

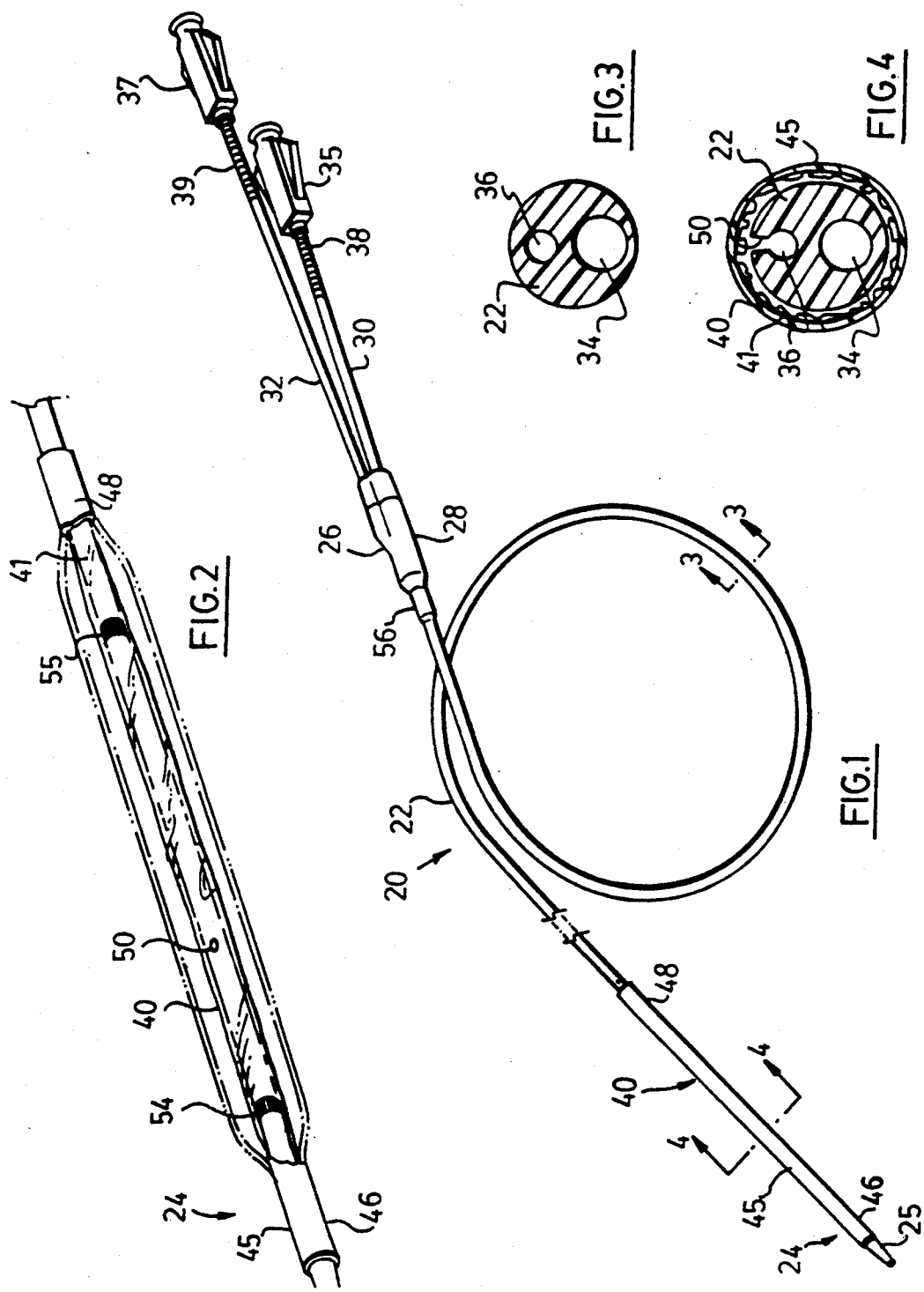

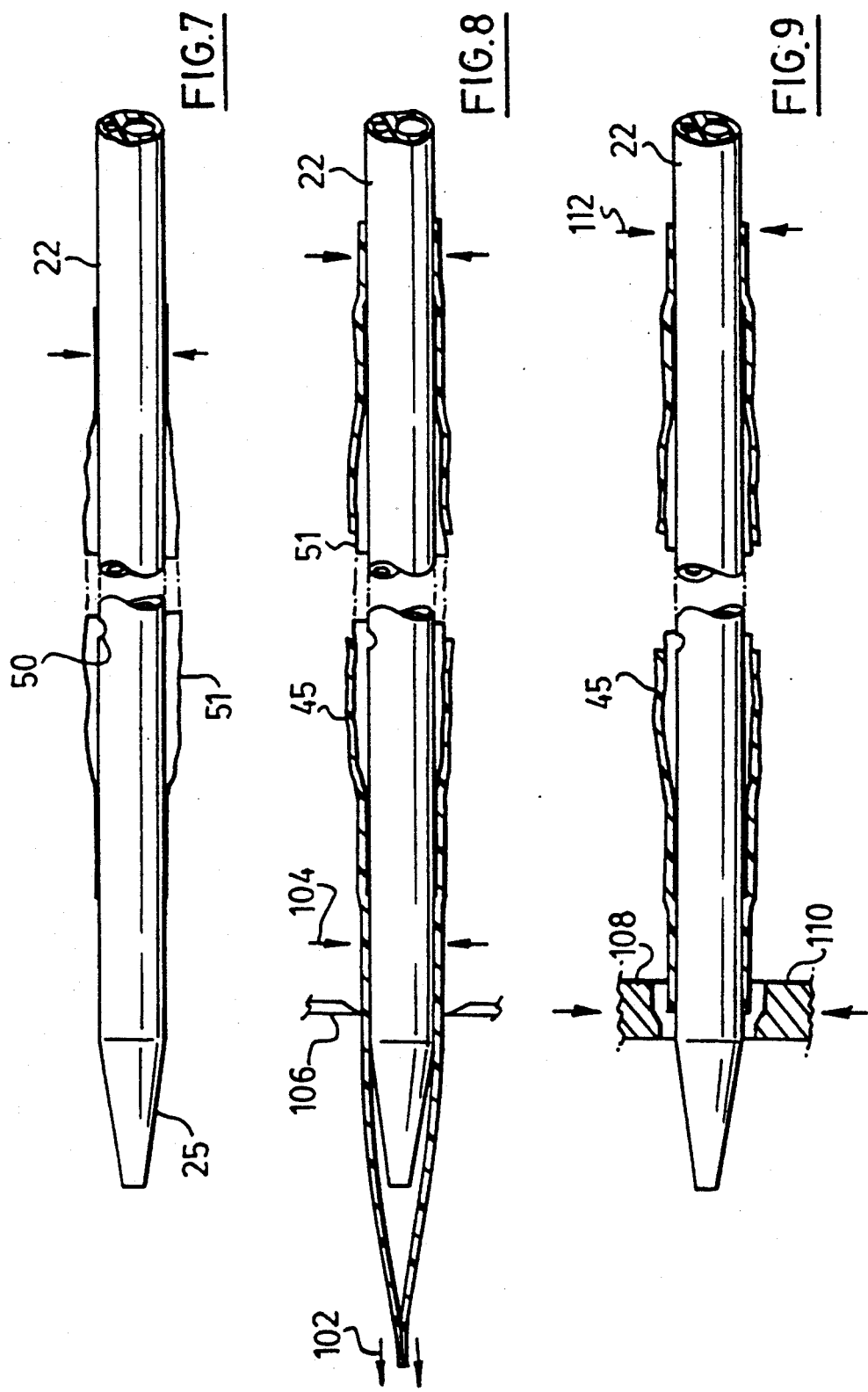

ANGIOPLASTY CATHETER WITH BALLOON RETAINER

DESCRIPTION

This invention relates to angioplasty catheters for use in the treatment of stenosed blood vessels. The invention also relates to a method of manufacturing the catheter.

BACKGROUND OF THE INVENTION

An angioplasty catheter is typically elongate and tubular, and is provided with a balloon near or at its distal end and radiopaque bands defining the extremities of the balloon. The catheter is inserted at a convenient location and fed into the stenosed blood vessel until the balloon is located in the narrowed portion of the blood vessel. Fluid from an external supply is then used to inflate the balloon such that it compresses the obstructing plaque and stretches the plaque coated walls of the blood vessel. When the physician is satisfied that the blood vessel has been widened sufficiently, the balloon is deflated and the catheter removed.

BACKGROUND ART

Angioplasty catheters have been successfully used for a number of years in the treatment of blood vessels obstructed or stenosed with plaque. An angioplasty catheter includes, near its distal end, a balloon which can be inflated by means of pressurized fluid supplied through a lumen in the catheter. The treatment involves the location of the balloon in the stenosed section of the blood vessel, followed by inflation and deflation. During inflation, the balloon compresses the plaque and stretches the blood vessel such that the cross-sectional area of the stenosis is increased until it is comparable to that of the unobstructed blood vessel. When the treatment has been completed the balloon is deflated and the catheter removed. The treated blood vessel maintains substantially its enlarged cross-section to permit the free flow of blood through this portion.

To perform satisfactorily a suitable angioplasty catheter must possess a number of properties. For ease of insertion it is preferable that the catheter is flexible, has a relatively small cross-sectional area, and has a smooth outer surface free of sudden changes in cross-section. Also, the method of insertion of the catheter has a significant bearing on the form of the catheter. The catheter which is the subject of the present invention is intended for insertion using the Seldinger technique and therefore preferably has a tapered distal end and a lumen to receive the Seldinger guide wire. The catheter ends at an aperture in the tapered end substantially coaxially with the main body of the catheter. However, perhaps the most important part of the catheter is the balloon which must be strong enough to withstand the application of high pressures without rupture and which must always inflate to a predetermined shape and size and then collapse for withdrawl. Also the balloon should be a continuous part of the catheter with flexibility to permit manipulation around bends as the catheter is inserted and withdrawn, and the structure supporting the balloon must give adequate support during all phases of use.

Another consideration in angioplasty catheters is the ease of use. It is preferable that the catheter can be inserted without the need to apply pressure or vacuum during insertion and it is also desirable to avoid the use of mechanisms for twisting the balloon or in other ways manipulating it prior to inflation at the site of the stenosed blood vessel. Also, after inflation, the balloon should be safe and free from defects which could cause explosion and fragmentation of the material.

One approach to providing a smooth catheter for improved insertion is found in U.S. Pat. No. 4,540,404 to Wolvek. In this intance a sheath is provided over the balloon forming a continuing surface with a tip portion so that a clean outer surface is provided during insertion. The sleeve must however be held in place during insertion to ensure that it does not separate from the tip and after insertion the sleeve is withdrawn along the catheter to expose the balloon in the vicinity of the stenosed blood vessel. The structure suffers from several disadvantages. First of all the sleeve must have significant thickness and this will increase the effective overall cross-section of the catheter resulting in possible difficulty inserting the catheter at the site of the stenosis. Further, the action of moving the sleeve may dislodge material from the site and leave it free to move in the blood stream and after using the balloon, the sleeve can not effectively be returned in its original position. As a result the catheter must be withdrawn with the exposed tip rubbing against the blood vessel walls.

Another approach is taught in U.S. Pat. No. 4,637,396 to Cook. This structure uses a laminated material for the balloon with the central of three layers being of knitted material having limited expansion characteristics to control the size of the balloon. Support is provided on a central flexible mandrel which would allow the balloon to be displaced relative to the main diameter of the catheter so that as the structure moves in a blood vessel, irregularities at bends would tend to deflect the balloon so that the resulting depression in the catheter would have to be overcome by the forces of insertion. Overall this structure is complicated, difficult to manufacture and does not present a continuous outer surface for smooth insertion due to the flexibility of the balloon and the possibility for deflecting the balloon as the catheter moves around bends.

Other attempts to produce catheters which solve some of the problems in the are taught in U.S. Pat. Nos. 4,338,942, 4,403,612, and 4,608,984 all of which issued to Thomas J. Fogarty. The structures use inner and outer balloons, the inner being inextensible, and the outer being elastic. Again the structure is such that in the vicinity of the balloon there could be some deflection during insertion and this is undesirable. Further, the structure requires the use of an external control to rotate the inner balloon into a stored position and there is no facility for use with a Seldinger wire.

SUMMARY OF INVENTION

The present invention provides an improved angioplasty catheter which does not suffer from the disadvantages noted in the prior art. The catheter has a main body including a tip and which extends from a proximal end to the tip at the distal end. The body defines a fluid supply lumen and a side opening providing communication with the lumen adjacent the tip. The lumen extends from the proximal end to the side opening and a balloon on the main body contains the opening for inflation and deflation. The balloon consists of a tubular inelastic membrane sealed to the body and a elastic sleeve over the membrane and attached at the ends, the sleeve being stressed to urge the balloon into a collapsed condition.

BRIEF DESCRIPTION OF THE DRAWINGS

FIG. 1 is a perspective view of an angioplasty catheter in accordance with a preferred embodiment of the present invention;

FIG. 2 is an enlarged isometric view of a balloon forming part of the catheter with portions broken away;

FIG. 3 is a sectional view on line 3—3 of FIG. 1;

FIG. 4 is a sectional view on line 4—4 of FIG. 1;

FIGS. 7 to 9 illustrate the assembly of the balloon and associated sheath on the catheter.

DESCRIPTION OF THE PREFERRED EMBODIMENT

Figure 5:
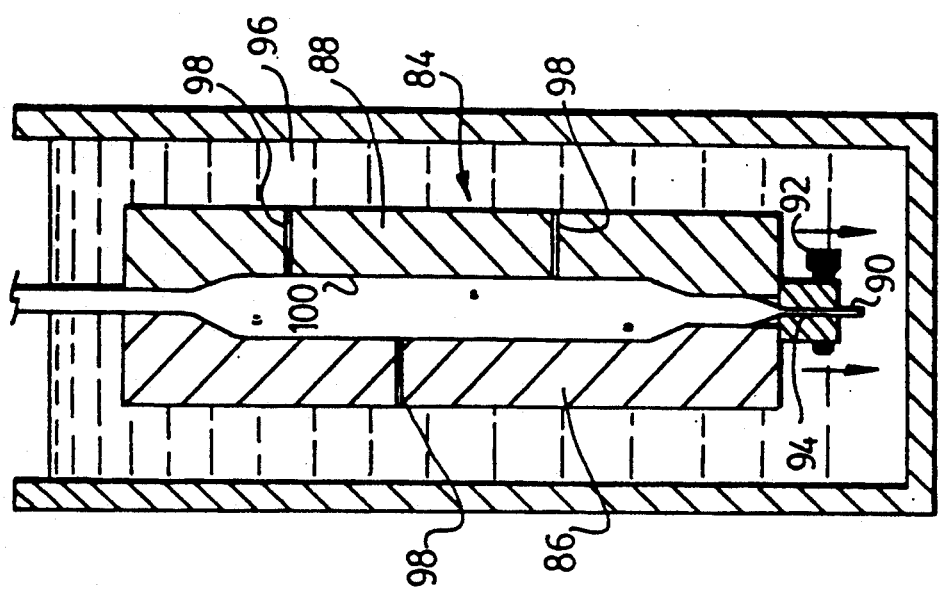
FIG. 5 is a diagrammatic sectional view illustrating the drawing of material to form a membrane used as part of the balloon.

The preferred embodiment of the angioplasty catheter according to the present invention will now be described in detail, firstly with reference to FIG. 1 of the drawings. This view shows an angioplasty catheter, designated generally by the numeral 20, including a flexible main body 22 having a distal end 24 defining a tapered tip 25 to facilitate insertion into a vein of a patient, and a proximal end 26 for connection, by means of connection piece 28, to the respective distal ends of a guide wire tube 30 and a fluid supply tube 32. The tubes 30, 32 are in communication with respective circular guide wire and fluid supply lumens 34, 36 defined within the main body 22 (FIG. 3) and are provided with luer fittings 35, 37 at the respective proximal ends. Different coloured marking sleeves 38, 39 help distinguish the tubes from one another (although in practice the fluid supply lumen 36 is of significantly smaller cross-section than lumen 34).

The body 22 extends from the connection piece 28 to the tip 24 and passes through a balloon 40, details of which are provided below. A tubular shipping protector (not shown) for location over the distal end 24 and balloon 40 would normally be provided to protect the balloon and to retain it in a collapsed condition ready for insertion.

Reference is now made to FIG. 2 of the drawings which shows the distal end of the catheter in greater detail with the balloon shown in a collapsed condition in full outline, and in an inflated condition in ghost outline. The balloon 40, located at the distal end 24, includes a Nylon membrane 41 which is flexible and substantially inextensible (i.e. not elastomeric) and, when inflated, is in the form of a cylinder having tapering ends (as indicated in ghost outline). The distal and proximal ends of the membrane locate snugly over the distal end 24 of the main body 22 with the distal end being mated to the body just short of the tapered tip 25. A side opening or aperture 50 in the wall of the main body 22 provides fluid communication between the smaller fluid supply lumen 36 and the interior of the balloon 40 between the body 22 and the membrane of the balloon. A sheath 45 of elastic material is stretched over the membrane 41 to complete the balloon. The sheath is attached at ends 46 and 48 to complete the assembly (as will be described later).

A pair of radiopaque strips 54, 55 are attached around the body 22 inside the balloon 40 and near the ends 46, 48 for monitoring the position of the balloon.

To inflate the balloon 40, fluid is supplied under pressure through the fluid supply tube 32 and the fluid supply lumen 36, and then through the aperture 50 into the balloon 40. Thus, the balloon is pushed radially outwardly by the fluid pressure to assume the shape shown by the chain-dotted lines in FIG. 3, so that the balloon 40 has a diameter greater than that of the main body 22. The membrane 41 controls the size and shape and energy is stored in the sheath 45. On deflation, and on withdrawing the fluid by suction (i.e. negative pressure) the energy in the sheath causes the membrane to fold and collapse to lie close to the outer surface of the body, as shown in FIG. 4 where, because of difficulties in drawing such thin material in section, the spacing between the sheath and body is exaggerated.

The membrane 41 (FIG. 1) is formed by a procedure illustrated diagrammatically in FIG. 5. A tube 56 of Nylon having a wall diameter thickness of about 0.015 inches is located in a copper mould 84 made up of two halves 86, 88. The tube 56 is cut at a lower end 90 and a clamp 92 is attached to a short end piece 94 which extends from the mould 84 to seal the end of the tube and to ensure that the tube is not pulled from the mould. The tube and mould are then suspended in a heated oil bath 96 at about 170° to 175° C. for three minutes. The total weight of the mould and accessories is about 150 gm and this weight tends to stretch the heated tube such that the molecular orientation becomes axial along the length of the tube.

After three minutes in the oil bath 96 a pressure of 400 p.s.i. is applied to the inside of the tube from an external supply (not shown) causing it to deform to occupy the interior of the mould, oil in the mould being pushed from the mould through relief holes 98. After a short interval of time the pressure is released and the mould containing the resulting membrane 100 is removed from the oil bath and placed in freon which acts as a coolant and disperses the oil. The membrane retains the tapered cylindrical shape of the mould, the deformed portion having a wall thickness in the order of 0.00025 to 0.0005 inches.

Figure 6:
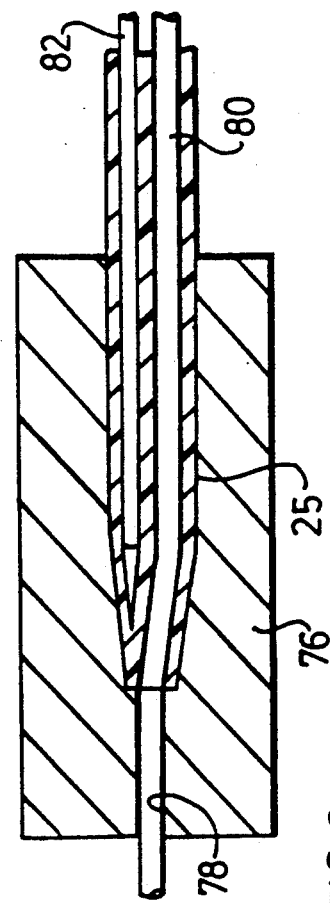
FIG. 6 is a sectional view illustrating the method of manufacturing a tip on the catheter.

The tip 25 (FIG. 1) is formed by a method shown in FIG. 6. A heated die 76 has an internal shape corresponding to that of the required tip and an opening 78 aligned with the tip to receive an end part of the mandrel 80 which is engaged through the guide wire tube of the body. A rod or mandrel 82 is provided in the fluid supply tube and, under the influence of heat from the die 76, the body is advanced into the die and deformed into the shape shown in FIG. 6. It will be seen in this Figure that the fluid supply tube has been terminated at its end whereas the guide wire tube has been retained in an open condition to provide access for the Seldinger wire during insertion. The form of the structure is such that the end is conical so that the Seldinger wire is centered relative to the catheter during insertion.

Reference is next made to FIG. 7 which illustrates one of the earlier steps in producing a balloon on the body 22 of the catheter. It will be seen that the membrane 51 has been slipped over the distal end of the catheter and positioned on the body 22. Arrows indicate where heated mandrels would be applied to seal the membrane to the body 22 at its ends. The inextensible membrane would lie quite smoothly against the body and this can not be drawn accurately which is why it is as shown in FIG. 7 for illustration purposes only.

After the FIG. 7 steps have been completed, a sleeve which is longer than the finished sleeve 45 indicated in FIG. 2, is slipped over the body until the proximal end is past the membrane. This end is then sealed in a similar fashion to that used for the membrane in the direction of the arrows and after this is completed, the membrane is stretched longitudinally as indicated by arrows 102 to apply some hoop stress which will tend to bring the membrane tightly into the body. With the sheath stretched in this fashion, heat and pressure are applied in the direction of arrows 104 to seal the sleeve in this condition where it will of course bring the membrane tightly into contact with the body 22. This can not be illustrated accurately.

After the sheath has been applied, excess material is cut by knives 106 and then to seal the ends of the sheath and make them smooth, heated dies 108, 110 are brought into position as shown in FIG. 9 and made to deform the end of the sleeve into a smooth contour with the body. This is repeated in the direction of arrows 112 to have a similar effect at the other end of the sheath.

The resulting balloon is supported on the body 22 which of course will be in some compression as a result of the tension applied to the sheath 45. Because the body is continuous with the remainder of the catheter, and because of the negligible resistance to bending in the balloon itself, the body of the catheter will move around contours in the blood vessels without impedance. Further, the profile of the balloon is very small and as a result it can be positioned in the stenosed portion of the blood vessel for subsequent inflation without disturbing the stenosis. On inflating, the membrane controls the size of the balloon and further energy is stored in the sheath so that when the pressure is disconnected, the sheath will bring the balloon back to its original position in close proximity with the body.

In the preferred embodiment the main body has an outside diameter of 5 French (about 0.0065 inches) with guide wire lumen about 0.037 inches and fluid supply lumen about 0.017 inches. The portion 56 (which corresponds to the original extrusion) is 7 French (about 0.090 inches), and the lumens 0.039 and 0.024 inches in diameter.

The sheath can be made from Latex (in which case a medical grade Epoxy would be used to attach it) Polyeurethane or Nylon materials such as PEBAX. The wall thickness of the sheath is in the order of 0.005 inches.

In use the catheter is entered conventionally using the Seldinger technique and the final location is found by monitoring the positions of the radiopaque strips 54, 55. Once in place the Seldinger wire is withdrawn, the balloon 40 is inflated by applying a pressurised fluid to the fluid supply lumen 34. This pressure overcomes the residual forces in the stressed sheath 45 and expands the balloon to compress plaque in the vein or artery. The balloon can be inflated until the membrane 41 is fully extended. After use, the pressure is released and stored energy in the sheath collapses the balloon and contains the membrane while presenting a relatively smooth and uninterrupted outer surface.

It will be evident that the structure described has advantages over the prior art in a number of ways. First of all the body is continuous and it is capable of being inserted using the Seldinger technique; the inextensible membrane is controlled against explosion and disintegration by the sheath which is sealed about it; the body is continuous throughout and in particular through the balloon to give support for the catheter as it is inserted. These and other advantages will be apparent from the invention.

The exemplary preferred embodiment described in the disclosure, and other embodiments are all within the scope of the invention as defined in the claims.

I claim:

1. An angioplasty catheter comprising:
   an elongate main body defining guide wire and fluid supply lumens and terminating at a distal end in a tapered tip, the fluid supply lumen being closed at the tip and the guide wire lumen extending to the tip for receiving a Seldinger wire to guide the catheter during insertion procedures, the main body defining a side opening meeting the supply lumen near the tip;
   a balloon sealed to the main body near the tip and containing said side opening, the balloon being of a membrane of inelastic material having a defined shape when inflated by fluid pressure applied through the supply lumen, and an elastic sheath covering the membrane;
   guide wire and fluid supply tubes; and
   a connection piece at the proximal end of said portion and connecting the tubes to said portion.

2. An angioplasty catheter as claimed in claim 1 in which the sleeve is in tension in the collapsed condition.

3. An angioplasty catheter as claimed in claim 1 in which the membrane is of Nylon with a thickness in the range 0.00015 to 0.0005 inches.

4. An angioplasty catheter comprising:
   a main body having a tip and extending continuously with a substantially constant cross-section from a proximal end to the tip at a distal end, the body defining a fluid supply lumen and a side opening providing communication with the lumen adjacent the tip, the lumen extending longitudinally from said proximal end to the side opening and terminating short of said distal end;
   connecting means attached to the body at the proximal end for connecting a fluid supply;
   a tubular non-elastic membrane sealed to the body to contain the side opening and to be inflated to a predetermined shape under the influence of pressurized fluid applied at the connecting means;
   a sleeve of elastic material sealed at the ends only to the assembly of the body and membrane and normally collapsed to hold the membrane in a stored condition tightly against the body, the sleeve storing energy as it is stretched when the membrane is inflated for use in collapsing the membrane and returning to the stored condition.

5. An angioplasty catheter as claimed in claim 4 in which the sleeve is in tension in the collapsed condition.

6. An angioplasty catheter as claimed in claim 4 in which the membrane is of Nylon with a thickness in the range 0.00015 to 0.0005 inches.

7. An angioplasty catheter as claimed in claim 4 in which the body further defines a guide wire lumen extending longitudinally from the proximal end to the distal end and terminating at the tip to provide access for using a Seldinger wire in the guide wire lumen.

8. An angioplasty catheter is claimed in claims 1, 4, 2 or 3 and further including radiopaque strips on the body and defining the extent of the balloon along the body.

9. An angioplasty catheter comprising:
   a main body defining a fluid supply lumen terminating at a side opening;

a balloon sealed to the main body about the side opening and including a non-elastic membrane having a predetermined shape when inflated and being collapsable about the body, and an elastic sleeve separated from the membrane and containing the membrane for urging the membrane from an inflated condition towards the collapsed condition; and means coupled to the body for attaching fluid supply means to inflate and deflate the balloon.

10. An angioplasty catheter as claimed in claim 9 in which the sleeve is in tension in the collapsed condition.

11. An angioplasty catheter as claimed in claim 9 in which the membrane is of Nylon with a thickness in the range 0.00015 to 0.0005 inches.

12. An angioplasty catheter as claimed in claim 9 in which the body further defines a guide wire lumen extending longitudinally from the proximal end of the distal end and terminating at the tip to provide access for using a Seldinger wire in the guide wire lumen.

13. A method of making an angioplasty catheter having a balloon as a main body and a fluid supply lumen in the main body and terminating at an aperture inside the balloon for inflating the balloon, the method characterised by the steps of placing an inelastic tubular membrane on the main body, and placing an elastic sheath over the membrane in a stressed condition with the ends of the membrane and sheath being attached to the main body so that the sheath retains the membrane in close proximity to the body before use and returns to this position after use.

* * * * *